United States Patent [19]

Wright et al.

[11] Patent Number: 5,201,880
[45] Date of Patent: Apr. 13, 1993

[54] MITRAL AND TRICUSPID ANNULOPLASTY RINGS

[75] Inventors: John T. M. Wright, Conifer; Donald P. Elliott, Denver, both of Colo.; Francis C. Wells, Sandy, England

[73] Assignee: Pioneering Technologies, Inc., Wheat Ridge, Colo.

[21] Appl. No.: 826,405

[22] Filed: Jan. 27, 1992

[51] Int. Cl.⁵ .............................. A61F 2/24
[52] U.S. Cl. .................................. 623/2
[58] Field of Search ........................ 623/2, 1

[56] References Cited

U.S. PATENT DOCUMENTS

| | | | |
|---|---|---|---|
| 4,042,979 | 8/1977 | Angell | 623/2 |
| 4,055,861 | 11/1977 | Carpentier et al. | 623/2 |
| 4,259,753 | 4/1981 | Liotta et al. | 623/2 |
| 4,290,151 | 9/1981 | Massana | 623/2 |
| 4,602,911 | 7/1986 | Ahmadi et al. | 623/2 |
| 4,917,698 | 4/1990 | Carpentier et al. | 623/2 |
| 5,061,277 | 10/1991 | Carpentier et al. | 623/2 |
| 5,064,431 | 11/1991 | Gilbertson et al. | 623/11 X |
| 5,104,407 | 4/1992 | Lam et al. | 623/2 |

Primary Examiner—David Isabella
Assistant Examiner—Dinh X. Nguygen
Attorney, Agent, or Firm—Grant L. Hubbard

[57] ABSTRACT

Adjustable, flexible mitral and tricuspid annuloplasty rings having internal drawstrings that emerge from the rings on the annular faces so that the drawstring knots are out of the bloodstream, the drawstrings being contained in clearly marked channels, the mitral ring having a curved semi-flexible stiffener member in the anterior segment to maintain intertrigonal distance during implantation, the plane of the anterior segment lying at an angle of about 30°-75° to the plane of the posterior segment, arcing up across the anterior leaflet to prevent outflow tract obstruction.

1 Claim, 5 Drawing Sheets

MITRAL AND TRICUSPID ANNULOPLASTY RINGS

BACKGROUND OF THE INVENTION

This invention relates to a prosthesis for use in the surgical correction of certain mitral or tricuspid valve disorders. There are two atrio-ventricular valves in the heart. That on the left side of the heart known as the mitral valve, and that on the right side known as the tricuspid valve. Both valves are subject to damage that requires that the valves be repaired or replaced. Clinical experience has shown that repair of the valve, where this is technically possible, produces better long term results than does valve replacement. The mitral and tricuspid valve differ significantly in anatomy. Whereas the annulus of mitral valve is somewhat "D" shaped, the annulus of the tricuspid valve is more nearly circular.

The effects of valvular dysfunction vary. Mitral regurgitation has more severe physiological consequences to the patient than does tricuspid valve regurgitation, a small amount of which is tolerated quite well. In patients with valvular insufficiency it is increasingly common surgical practice to retain the natural valves, and to attempt to correct the defects. Many of the defects are associated with dilation of the valve annulus. This dilatation not only prevents competence of the valve but also results in distortion of the normal shape of the valve orifice. Remodelling of the annulus is therefore central to most reconstructive procedures on the mitral valve.

Many procedures have been described to correct pathology of the valve leaflets and their associated chordae tendinae and papillary muscles. In mitral repairs it is essential to preserve the normal distance between the two fibrous trigones. The trigones almost straddle the anterior leaflet portion of the annulus. Between the left and right fibrous trigones the mitral annulus is absent (as described by Tsakiris AG. "The physiology of the mitral valve annulus" in The mitral valve-a pluridisciplinary approach. ed Kalmanson D. Publishing Sciences Group, Acton, Mass. 1976, pg 21-26). This portion of the mitral valve apparatus is formed by the change of the anterior portion of the base of the aorta into the (so called) sub-aortic curtain, and hence into the anterior leaflet of the mitral valve. A significant surgical diminution of the inter-trigonal distance could cause left ventricular outflow obstruction. Thus it is highly desirable to maintain the natural inter-trigonal distance during and following mitral valve repair surgery. Consequently, when a mitral valve is repaired (be it the posterior or anterior leaflet) the result is generally a reduction in the size of the posterior segment of the mitral valve annulus.

As a part of the mitral valve repair it is either necessary to diminish (i.e. constrict) the involved segment of the annulus so that the leaflets may coapt correctly on closing, or to stabilize the annulus to prevent post-operative dilatation from occurring. Either is frequently achieved by the implantation of a prosthetic ring in the supra annular position. The purpose of the ring is to restrict and/or support the annulus to correct and/or prevent valvular insufficiency. However, it is important not to over restrict the annulus or an unacceptable valvular stenosis would result. As described above, in mitral valve repair, constriction of the mitral annulus should take place only in the area of the posterior section of the valve annulus. Shortening of the posterior portion of the mitral valve annulus may be accomplished in several ways. Firstly, by implanting a substantially inexpansible ring (smaller in size than the annulus). With this type of device, the surgeon must accurately choose the size of ring that will just prevent insufficiency, yet will not cause significant valvular stenosis. Secondly, by a using a contractable ring that may be plicated during implantation. This type has the disadvantage that the surgeon must then accurately judge not only the ring size to use, but also how to space the implanting sutures in the ring and the annulus so that when implanted, insufficiency is minimized, yet there will be no significant valvular stenosis. Thirdly, and preferably, by a substantially inexpansible ring that may be contracted only in appropriate segments (and not in the anterior portion). The natural inter-trigonal distance should be maintained, and the anterior leaflet should not be diminished in circumference.

In tricuspid valve repair, constriction of the annulus usually takes place in the posterior leaflet segment and in a small portion of the adjacent anterior leaflet. The septal leaflet segment is not usually required to be shortened.

Various prostheses have been described for use in conjunction with mitral or tricuspid valve repair. Each has disadvantages. The ring developed by Dr. Alain Carpentier (U.S. Pat. No. 3,656,185) is rigid and flat. Although widely used, criticism of its inflexibility preventing the normal alteration in size and shape of the mitral annulus with the cardiac cycle has been widespread. The complication of left ventricular outflow tract obstruction has been described in association with this device. This complication can take the form of a decrease in the dimensions of the left ventricular outflow tract, or systolic anterior motion of the anterior leaflet of the valve. Both complications were reported by Geller M, Kronzon I, Slater J et al. "Long-term follow-up after mitral valve reconstruction: incidence of postoperative left ventricular outflow obstruction". Circulation 1986;74(suppl I) I-99-103. They implanted Carpentier rings in sixty-five patients. All sixty surviving patients were restudied 1-55 months postoperatively. All showed a significant decrease in the dimensions of the left ventricular outflow tract, and 6 patients (10%) also had systolic anterior motion (SAM). Another complication of the Carpentier ring has been inflow obstruction. This complication associated with its use in tricuspid valves was reported by Carpentier et al. in nine of seventeen patients (Carpentier A, Deloche A, Hanania G, et al. "Surgical management of acquired tricuspid valve disease". J Thorac Cardiovasc Surg 1974;67:53-65). In addition, the Carpentier ring has the disadvantage of not being of adjustable size. Thus the surgeon has to accurately judge the correct size of ring needed to reduce the annulus size and produce a competent valve.

An open ring valve prosthesis was described in U.S. Pat. No. 4,164,046 comprising a uniquely shaped open ring valve prosthesis having a special velour exterior for effecting mitral and tricuspid annuloplasty. This ring was not adjustable in size during or following implantation. The fully flexible annuloplasty ring described by Carlos D. Duran and Jose Luis M. Ubago, "Clinical and Hemodynamic Performance of a Totally Flexible Prosthetic Ring for Atrioventricular Valve Reconstruction" Annals of Thoracic Surgery, (No. 5), 458–463, (November 1976) could only be shortened in the posterior segment by the placement of plicating sutures. The judgement of the position, size and spacing of these sutures requires skill and experience. However, inappropriate suture placement in the anterior segment could cause undesirable intra-trigonal shortening. Adjustable annuloplasty rings were described by Dr. William Angell (U.S. Pat. No. 4,042,979) and Dr. Miguel Puig-Massana (U.S. Pat. No. 4,290,151). Both incorporate draw-strings capable of reducing the size of the posterior portion of the ring. The former contains a rigid or flexible member in the anterior leaflet portion of the ring. The latter ring is also adjustable but fully flexible. With this device the use of a continuous implantation suture was recommended rather than the more generally used interrupted sutures. With the Puig-Massana ring the use of interrupted sutures would be likely to interfere with the internal drawstrings. However, should a continuous suture be used for implantation, and the ring then contracted by the internal drawstrings, loosening of the continuous suture would be caused by the reduction in the circumference of the annulus. A further disadvantage of Puig-Massana's ring is that following the tightening of the drawstrings, a bulky knot is formed on the atrial surface of the ring. Hence, the knot lies in the direct blood flow path into the inflow of the valve. Should a thrombus form on the knot it could later embolize. In addition, should the surplus drawstrings be cut too close to the knot, there is the danger of the knot becoming undone. Conversely, should significant surplus drawstrings tails remain, abrasion of the valve leaflets could occur. The adjustable ring by Dr. Ali Ahmadi has the disadvantage of being circular, which is not an appropriate shape, particularly for the mitral annulus.

The rigid rings described above were probably conceived on the assumption that the mitral annulus is "D" shaped and lies in a single flat plane. That this was a misconception was shown by Levine, R. A., Triulzi, M. O., Harrigan P., and Weyman, A. E. "The relationship of mitral annular shape to the diagnosis of mitral valve prolapse", Circulation 75, No. 4, 756–767, 1987. This work shows that the mitral valve annulus is a complex and mobile structure and demonstrated that the mitral valve takes the form of a central, elliptical portion of a hyperbolic paraboloid or saddle shaped surface. It is clear that imposing a flat ring or even a segment of a flat ring would distort the annulus and could cause left ventricular outflow tract obstruction. The device which is the subject of this invention does not have these disadvantages.

SUMMARY OF THE INVENTION

This invention relates to adjustable and flexible atrioventricular annuloplasty rings containing circumferential radiopaque markers with mitral and tricuspid valve variations specific to their varying requirements. The variant of the ring for use in the mitral region incorporates a curved framework in the anterior segment. The framework member is to maintain the intratrigonal and anterior leaflet distance during implantation. It is curved to prevent aortic outflow tract obstruction. Two pairs of drawstrings allow adjustment of four segments of the posterior portion of the mitral valve annulus. The variant of the ring for use in the tricuspid region incorporates a single pair of drawstrings to allow adjustment of the posterior left and right segment of ring at implantation. The flexible contractile body of the ring common to both variants is of a biocompatible cloth, preferably of a braided polyethertetraphylate tubular material, joined and folded in a particular manner that produces a eight walled body. The body is substantially oval in cross-section. The use of a braided material allows the ring the ability to contract under the action of the drawstrings without bunching.

It is an objective of this invention to provide flexible, adjustable annuloplasty rings specific for use in mitral and tricuspid valve repair.

It is a further objective of this invention to provide an annuloplasty ring that may be adjusted in the required segments of the annulus.

It is a further objective of this invention to provide a mitral annuloplasty ring in which the inter-trigonal distance and anterior segment is maintained during implantation.

It is a further objective of this invention to provide an annuloplasty ring that may be adjusted in diameter by means of internal drawstrings during implantation to eliminate or minimize valvular regurgitation.

It is a further objective of this invention to provide an annuloplasty ring that in preferred embodiments the drawstring tie knots do not lie in the main blood flow path.

It is a further objective of this invention to provide an annuloplasty ring that will allow the surgeon to correct certain technical errors that might have occurred during implantation.

It is a further objective of this invention to provide a mitral annuloplasty ring that is flexible (in an undulating manner) so as to follow the change in shape of the mitral annulus, in the plane of the annulus.

It is a further objective of this invention to provide a mitral annuloplasty ring that is flexible about the posterior portion of its circumference, and that prevents restriction of the left ventricular outflow tract.

It is a further objective of this invention to provide a mitral annuloplasty ring that is capable of selective adjustable restriction in the posterior leaflet segments.

It is a further objective of this invention to provide a tricuspid annuloplasty ring that is capable of adjustable restriction in the posterior leaflet segment.

It is a further objective of this invention to provide an annuloplasty ring that is technically easy to use.

It is a further objective of this invention to provide an annuloplasty ring that is capable of being implanted and adjusted in a relatively short time.

It is a further objective of this invention to provide an annuloplasty ring that is radiopaque around its entire circumference. Other objectives and advantages of this invention will be more apparent from the detailed description of the device which follows.

BRIEF DESCRIPTION OF THE DRAWINGS

The present invention may be better understood and the advantages will become apparent to those skilled in the art by reference to the accompanying drawings, wherein like reference numerals refer to like elements in the several figures, and wherein.

DESCRIPTION OF THE PREFERRED EMBODIMENT

This invention is directed to adjustable and flexible atrio-ventricular annuloplasty rings containing circumferential radiopaque markers with one preferred embodiment for use in mitral valve and a second preferred embodiment for use in tricuspid valve repair. Adjustment of the ring is achieved by means of internal drawstrings. To avoid the presence of a bulky knot on the inflow aspect of the rings, the drawstring exit points are preferably located on the face of the ring which lies adjacent to the tissue annulus. Hence, when the drawstrings are tightened and pairing ends are tied together, the knots are formed between the annulus and the ring, out of the direct blood flow.

In the preferred embodiment of the invention intended for use in the mitral valve, the flexible, contractile portion of the prosthesis is formed to fit about the base of the posterior leaflet of the valve. Two pairs of drawstrings are located in the posterior segment of the ring to allow adjustment of four segments of the posterior portion of the mitral valve annulus. A curved framework member located in the anterior portion of the prosthesis is to maintain the natural geometry of the anterior segment during implantation. It is shaped to follow a curved path on an inclined plane on the sub aortic curtain above the so called annulus of the anterior leaflet. Colored trigone markers in the anterior segment are used as sizing and implanting guides. When the mitral annuloplasty ring is secured into position about the valve, the two portions of either or both of the drawstrings located in the posterior segment of the valve annulus may be tightened if required to halt or minimize any residual valvular insufficiency. Drawstring tightening may be made individually or together in pairs to minimize any remaining insufficiency. This fine tuning capability allows a larger, rather than a smaller ring to be implanted and then the size optimally reduced.

In the preferred embodiment of the invention intended for use in the tricuspid valve, the prosthesis is flexible around its circumference and is formed to fit about the base of the valve leaflets. A contractable portion of the prosthesis is formed to fit about a substantial portion of the base of the posterior segment, and may extend into a insubstantial portion of the base of the anterior segment of the valve annulus. This contractable segment incorporates a pair of drawstrings to allow adjustment of a substantial segment of posterior annulus and an insubstantial segment of the anterior annulus at implantation. When the tricuspid variant is secured into position about the valve, the two portions of the drawstring located in the posterior segment of the valve annulus may be tightened if required. Tightening may be individually or together to minimize any remaining insufficiency. This fine tuning capability allows a larger, rather than a smaller ring to be implanted and then the size optimally reduced.

The flexible contractable body of the ring common to both variants is of a biocompatible cloth, preferably of a braided polyethertetraphylate tubular material. During construction of the ring, the tubular braid is cut to length and invaginated to form a double walled tube having a roll over fold at one end, and the two cut ends at the other. The two walls of the tube are heat sealed (welded) together close to the two cut ends and at an appropriate distance from the folded end using a heated knife. This heat seal forms a circumferential weld around the tube. The tube is then rolled so that the weld line will lie substantially centrally in the inner wall of the tube. The tube is then heat set into a "V" configuration. This configuration produces an eight walled flexible contractile member when the annuloplasty ring is completed. Two of the many steps in the completion of the ring include the sewing of the folded ends together to form a radial seam, and sewing of the apices of the "V" together to form a circumferential seam. Various components, such as drawstrings, stiffener and radiopaque markers are conveniently placed within and/or sewn in the "V" form before the circumferential seam is completed. This construction method produces an annuloplasty ring that is relatively simple to manufacture, yet contains drawstrings to provide adjustability, radiopaque markers for postoperative assessment, and a semi-flexible member in the anterior portion of the mitral variant to maintain the natural geometry of the intra-trigonal and anterior leaflet distance. At the same time it provides adequate strength and flexibility, yet permits a low needle penetration force for convenience of implantation. A particular advantage of this construction is that there are no portions of the textile material that might fray, and that the weld line is to placed within the ring is both inconspicuous and not subject to undue stresses. The body is substantially oval in cross-section.

Figure 1:
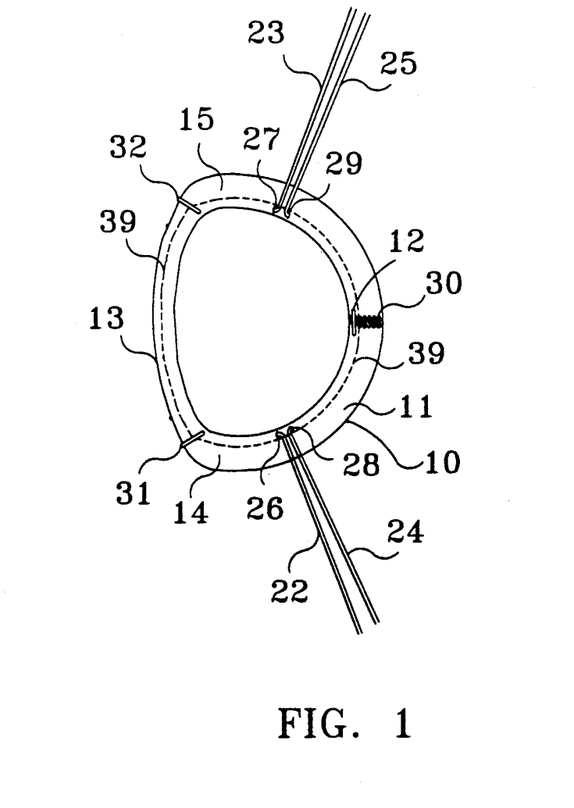
FIG. 1 shows a plan view from the tissue annulus aspect of the preferred embodiment of the ring intended for the mitral valve.
Figure 2:
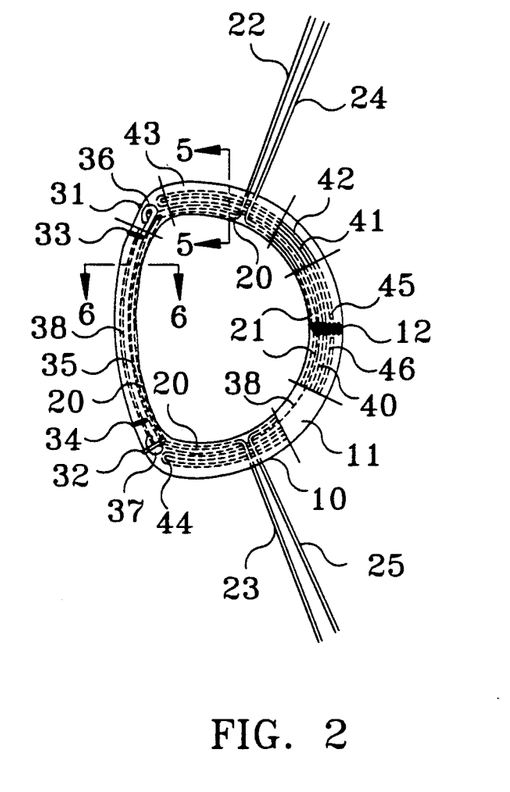
FIG. 2 shows a plan view from the atrial aspect of the preferred embodiment of the ring intended for the mitral valve.
Figure 3:
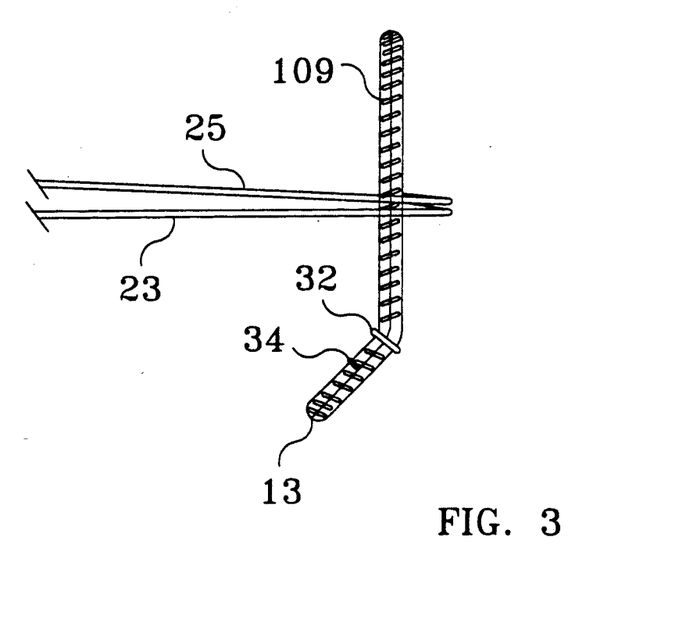
FIG. 3 shows a side view of the preferred embodiment of the ring intended for mitral valve repair.
Figure 4:
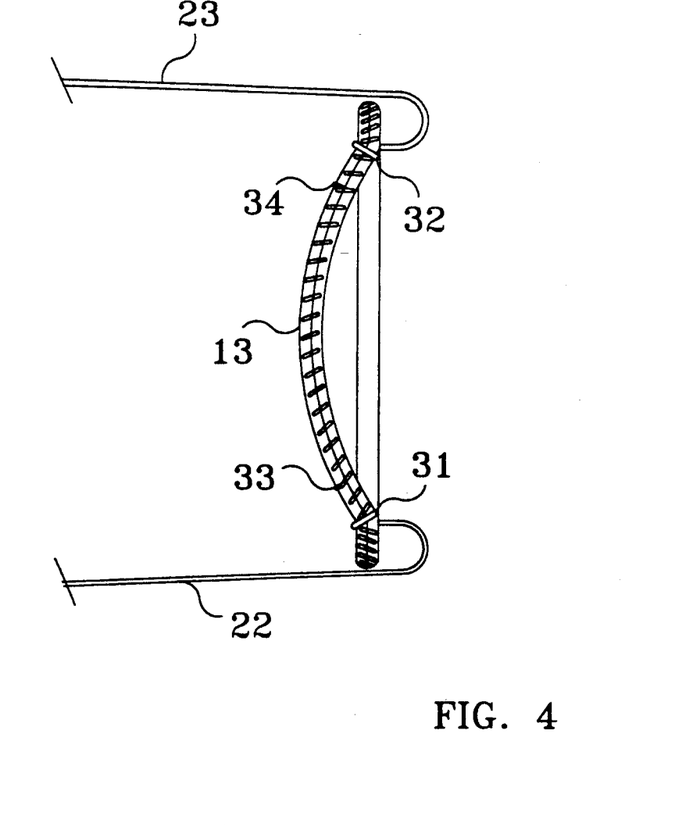
FIG. 4 shows a end view of the preferred embodiment of the ring intended for mitral valve repair.
Figure 5:
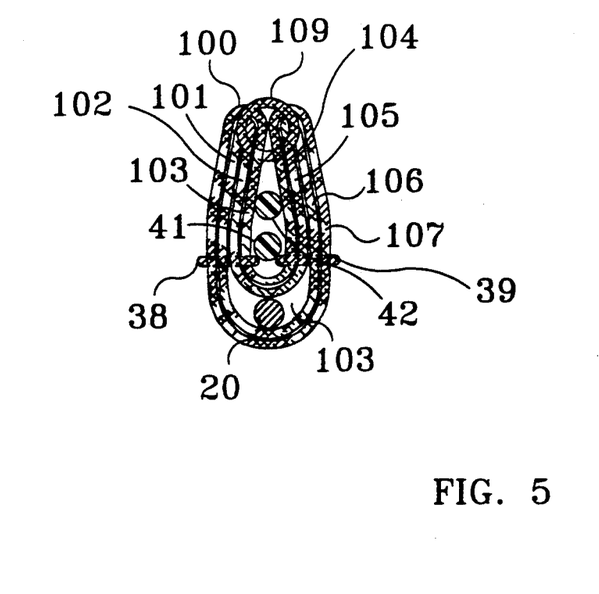
FIG. 5 shows a cross-sectional view taken along line AA of FIG. 2.
Figure 6:
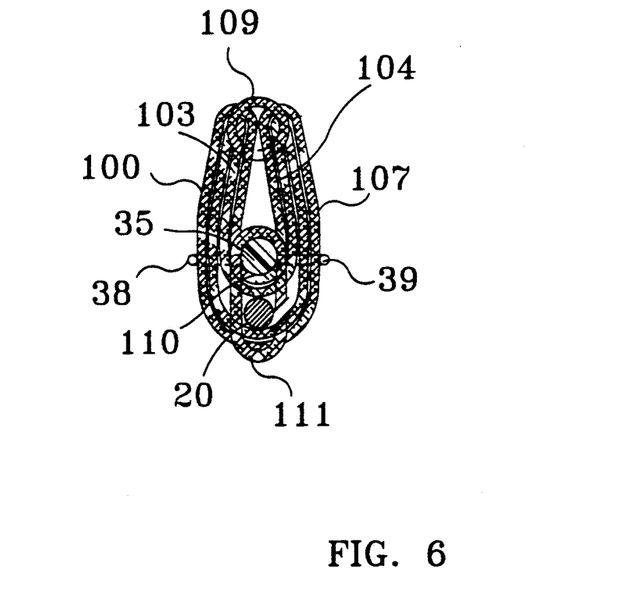
FIG. 6 shows a cross-sectional view taken along line BB of FIG. 2.

Referring to the drawings wherein like numerals indicate like elements there is shown in FIG. 1 and FIG. 2 plan views (from the annulus and atrium aspects respectively) of the preferred embodiment of a flexible, adjustable annuloplasty ring intended for the mitral valve designated as 10. FIG. 3 shows a side view and FIG. 4 shows an end view of the preferred embodiment of the variant of the ring intended for the mitral valve. FIG. 5 shows a cross-sectional view taken along line AA of FIG. 2. FIG. 6 shows a cross-sectional view taken along line BB of FIG. 2.

The device is composed of a tubular body of textile nature 11, which has its folded ends sewn together at seam 12 to form a ring. The ring has three segments, the anterior segment 13, the right posterior segment 14, and the left posterior segment 15. In the interior of tubular body 11 are provided filiform strings 20, 21, which have external portions 22, 23, 24, 25. These strings, which are preferably of a braided polyester surgical suture, emerge from the annulus face of the ring at exit points 26, 27, 28, 29 respectively. The distance between exit points 26 and 28 are approximately 3 mm. The distance between exit points 27 and 29 is similar.

The strings are anchored to the ring at points 30, 31, and 32. Points 33 and 34 are colored markers sewn onto the upper (atrial) surface of the ring that are intended as guides for implantation. These points are intended to lie adjacent to the right and left fibrous trigones of the mitral annulus. Also at implantation, point 31 will approximately correspond to the junction of the anterior leaflet and the right commissural leaflet of the mitral annulus. Point 32 will approximately correspond to the junction of the anterior leaflet and the left commissural leaflet. An internal curved flexible member 35 spans the area corresponding to the anterior segment of the mitral annulus from points 31 to 32, and has a closed loops 36, 37 at its ends. Drawstring 20 is passed through these loops and through the walls of body 11 to form part of the anchor knots at 31 and 32. Drawstring 21 is passed through the walls of body 11 to lie externally for a short distance 30 and is tied internally to form the anchor knot laying under external portion 30.

The framework member 35 is preferably of a corrosion resistant metal wire with good flexure fatigue resistance such as Carpenter MP35N alloy or Elgiloy. These alloys may be aged by heat treatment following cold working. This is an advantage over other corrosion resistant materials such as titanium alloys, because aging significantly improves the yield strength and the fatigue strength.

A colored demarcation suture line 38 on the upper (atrial) surface of the ring body indicates to the surgeon a line, outside of which the implanting sutures must be placed to avoid interference with the internal drawstrings or the stiffener member. A corresponding, but preferably uncolored, demarcation suture line 39 is situated on the lower (annulus) surface of the ring body. A flexible radiopaque member 40, is contained within body 11, in the posterior region between drawstring anchor points 31 and 32. This member, in conjunction with metallic stiffener 35, forms a circumferential X-ray marker. Member 40 may conveniently be composed of a single continuous length of 0.020" diameter extruded silicone rubber impregnated with 55% Barium Sulfate and 6% Tungsten. Material of this composition and diameter is sufficiently radiopaque, but does not unduly impede the passage of the needles of the implanting sutures. It has elements 41, 42, "hairpin" bends 43, 44, and ends 45, 46. The "hairpin" bends 43, 44, lie adjacent to loops 36, 37 respectively, and ends 45, 46 lie adjacent to seam 12.

FIG. 5 shows a cross-sectional view taken along line AA of FIG. 2. Cloth layers 100, 101, 102, 103, 104, 105, 106, 107 are formed from a singular tubular braided length of material folded and joined as previously described. The four cloth layers, when folded and heat set, form an upper (atrial) surface 100, and a lower surface 107 that will lie on the natural annulus. Colored demarcation stitch 38 passes from cloth layer 100, through layers 101, 102, 103 and hence back to layer 100. The second demarcation stitch 39, which is preferably uncolored (white), is similarly passed from cloth layer 107, through layers 106, 105, 104 and hence back to layer 107. Demarcation sutures 38, 39 passing through their respective cloth layers delineate channel 108 which contains drawstring 20 (or 21). Radiopaque marker member portions 41, 42 are enclosed between cloth layers 103, 104. A helical, continuous, circumferential sewn seam 109 joins cloth layers 100, 101, 102, 103 to corresponding cloth layers 107, 106, 105, 104.

FIG. 6 shows a cross-sectional view taken along line BB of FIG. 2. Framework member 35 is retained along its length against the fold 110 of the cloth layer 103, 104 by a continuous helical thread 111.

Figure 7:
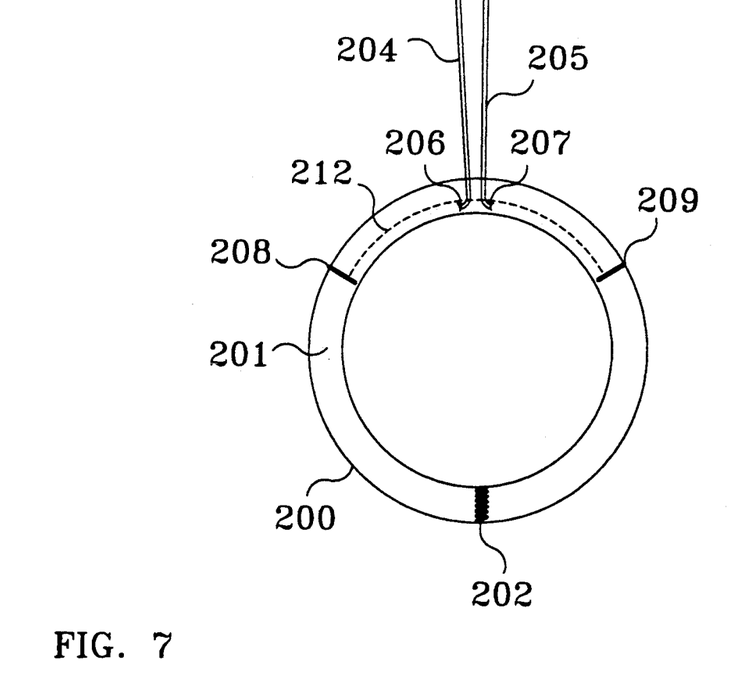
FIG. 7 shows a plan view from the tissue annulus aspect of the preferred embodiment of the ring intended for the tricuspid valve.
Figure 8:
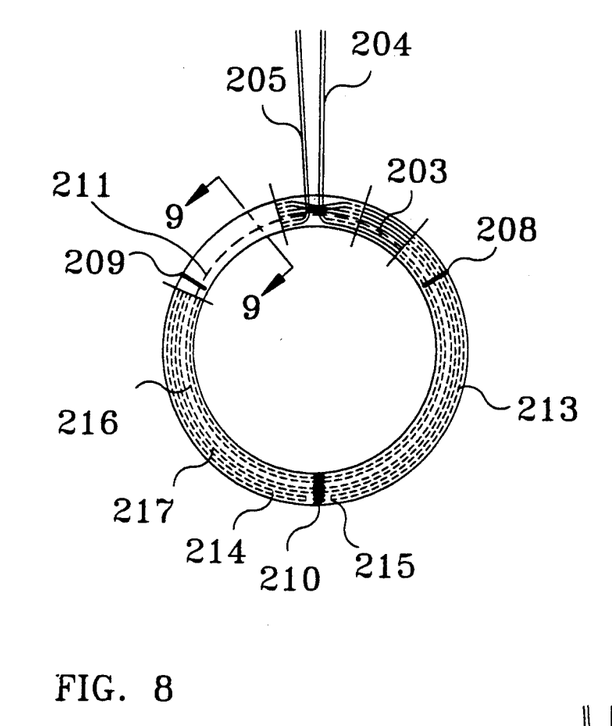
FIG. 8 shows a plan view from the atrial aspect of the preferred embodiment of the ring intended for the tricuspid valve.
Figure 9:
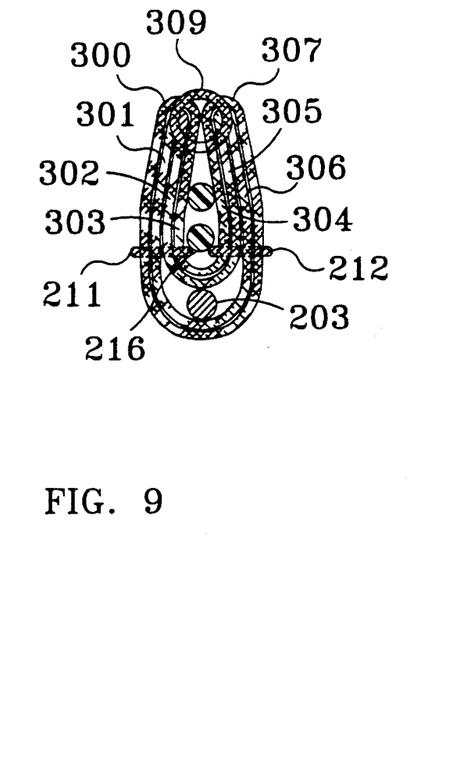
FIG. 9 shows a cross-sectional view taken along line AA of FIG. 8.

FIG. 7 and FIG. 8 show plan views (from the annulus and atrial aspects respectively) of the preferred embodiment of a flexible, adjustable annuloplasty ring intended for the tricuspid valve designated as 200. FIG. 9 shows a cross-sectional view taken along line AA of FIG. 8. The device is composed of a tubular body of textile nature 201, which has its folded ends sewn together at seam 202 to form a ring. In the interior of tubular body 201 is provided a filiform string 203 which has external portions 204, 205. This string, which is preferably of a braided polyester surgical suture, emerges from the annulus face of the ring at exit points 206, 207. The distance between exit points 206 and 207 is approximately 3 mm. The string also emerges from, passes around the body (208, 209) and reenters the body 201 at the drawstring anchor points. The string is anchored in the ring by internal looped knots adjacent to external loops 208, 209.

A colored marker 210 is sewn onto the upper (atrial) surface of the ring. This is a guide to the surgeon, indicating the point that should be positioned adjacent to the junction of the septal and anterior leaflet at implantation. A colored demarcation suture line 211 on the upper (atrial) surface of the ring body indicates to the surgeon a line, outside of which the implanting sutures must be placed to avoid interference with the adjustable segments of the internal drawstring 203. A corresponding, but preferably uncolored, demarcation suture line 212 is situated on the lower (annulus) surface of the ring. A flexible member 213, is contained within body 201. This member forms a circumferential radiopaque marker. It may conveniently be composed of a single length of 0.020" diameter extruded silicone rubber impregnated with 55% Barium Sulfate and 6% Tungsten. This member 213, having ends 214, 215 lying adjacent to seam 202 passes twice around the circumference of the ring to form concentric members 216, 217.

FIG. 9 shows a cross-sectional view taken along line AA of FIG. 8. Cloth layers 300, 301, 302, 303, 304, 305, 306, 307 are formed from a singular tubular braided length of material folded and joined as previously described. The four layers, when folded and heat set, form an upper (atrial) surfaces 300, a lower surface 307 that will lie on the natural annulus. Colored demarcation stitch 211 passes from cloth layer 300, through layers 301, 302, 303 and hence back to layer 300. A second demarcation stitch 212, which is preferably white, is likewise passed between cloth layer 307, through layers 306, 305, 304 and hence back to layer 308. Demarcation sutures 211, 212 passing through their respective cloth layers delineate channel 308 which contains drawstring 203. Radiopaque marker member elements 216, 217 are enclosed between cloth layers 303, 304. A helical, continuous, circumferential sewn seam 309 retains cloth layers 300, 301, 306, 307 together.

Figure 10:
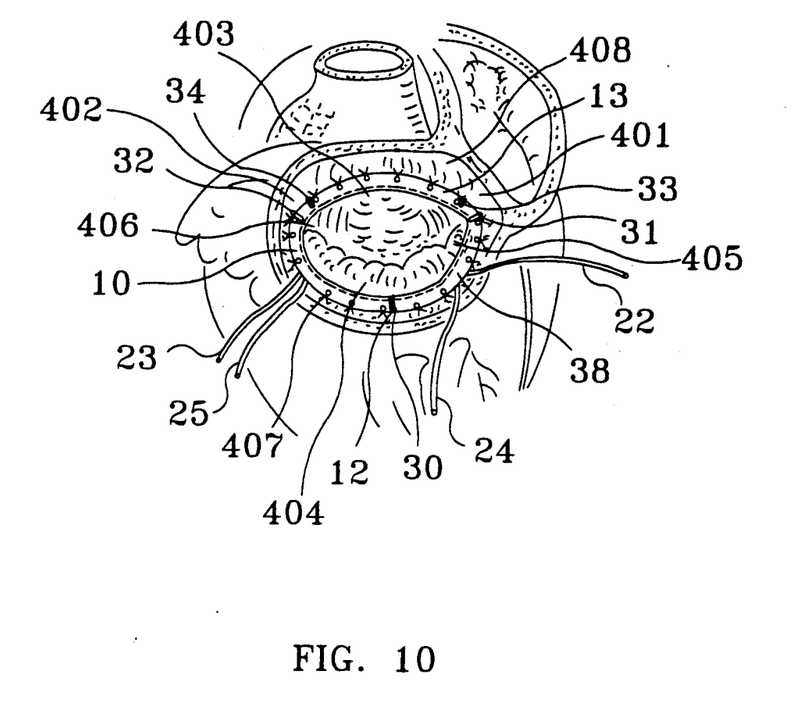
FIG. 10 shows an isometric view of the preferred embodiment of the ring for mitral valve repair sewn onto the mitral annulus of the heart.

FIG. 10 shows an isometric view of the preferred embodiment of the ring for mitral valve repair sewn onto the mitral annulus of the heart (the left atrium is removed for clarity of illustration). The heart is shown during ventricular systole (i.e. the mitral valve is closed and the left ventricular outflow tract is pressurized). The annuloplasty ring 10, is positioned such that colored markers 33, 34, are coincident to the right fibrous trigone 401 and left fibrous trigone 402 of the mitral valve apparatus. The anterior leaflet 403 is shown coapting to the posterior leaflet 404. Seam 12 will lie approximately at the midpoint posterior portion of the annulus. Drawstring anchor point 31 is located on the annulus approximately at the junction of the anterior leaflet and the right commissural leaflet, 405. Likewise, drawstring anchor point 32 is located on the annulus approximately at the junction of the anterior leaflet and the left commissural leaflet, 406.

The curved anterior portion of the ring 13 containing the internal curved framework member spans the anterior segment of the mitral annulus 403 from points 31 to 32, and the plane of segment 13 lies at an angle of approximately 45°–85° to the plane of the remainder of the ring. A colored demarcation suture line 38 on the upper (atrial) surface of the ring body indicates to the surgeon a line, outside which the implanting sutures 407 must be placed to avoid interference with the internal drawstrings or the stiffener member. Numerous interrupted sutures 407, are used to fix annuloplasty ring to the mitral valve annulus and to the sub aortic curtain 408. External portions of the drawstrings 22, 23, 24, 25 may be tightened and tied to the adjoining drawstring to constrict the ring where required to correct or minimize valvular insufficiency. The act of drawing in either or both drawstrings 22, 24 and or 23, 25 will cause the ring to contract between the drawstring anchor points 30 and 31 or 30 and 32 respectively. The amount of contraction will depend upon how much each drawstring is tightened, and whether only one, two, three or all four drawstrings are tightened. By such means the circumference of the annulus may be further reduced to correct or minimize any remaining valvular insufficiency following ring implantation.

Figure 11:
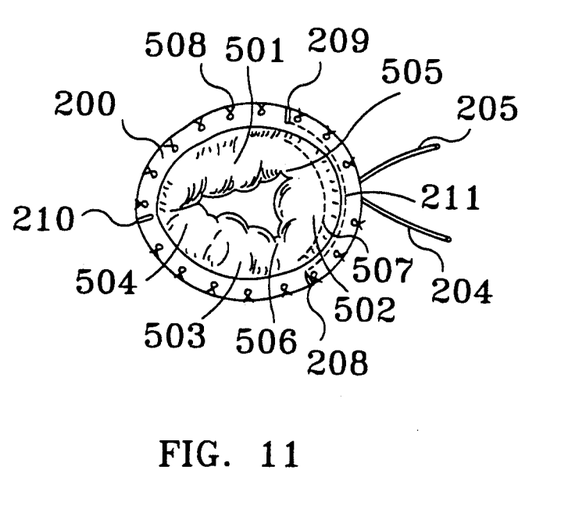
FIG. 11 shows a plan view of the preferred embodiment of the ring for tricuspid valve repair sewn onto a typically enlarged tricuspid annulus and insufficient tricuspid valve of the heart.

FIG. 11 shows a plan view of the preferred embodiment of the invention for tricuspid valve repair sutured in place in the typically enlarged tricuspid annulus (as described by Bex JP and Lecompte Y. "Tricuspid valve repair using a flexible linear reducer", J Cardiac Surg, 1:151, 1986). The tricuspid valve has an anterior leaflet 501, a posterior leaflet 502 and the septal leaflet 503. The junction of the septal and anterior leaflets is 504, the junction of the anterior and posterior leaflets is 505, and the junction of the posterior and septal leaflets is marked 506. The dotted line 507 shows the circumference of the annulus before pathologic dilatation.

The annuloplasty ring 200, is positioned such that colored marked 210 is approximately coincident with junction 504. Numerous interrupted sutures 508, are used to fix annuloplasty ring to the tricuspid valve annulus. The adjustable segment is delineated from drawstrings anchor points 208 to 209. Typically, this adjustable segment will approximately straddle a substantial portion of the posterior leaflet 502, as well as the junction of the posterior and anterior leaflets 505. It may also straddle an insubstantial portion of the anterior leaflet 501. The act of drawing in either or both drawstrings 204, 205 will cause the ring to contract between the drawstring anchor points 208 and 209. The amount of contraction will depend upon how much the drawstring is tightened, and whether only one or both drawstrings are tightened. By such means the enlarged circumference of the annulus may be reduced to that shown by dotted line 507. Following appropriate reduction the downstring pairs are tied using a surgeon's knot which will lie between the ring and the annulus, out of the bloodstream.

The method of use of is as follows. The left atrium is exposed following a mid-line sternotomy, and cardiopulmonary bypass established using conventional techniques. A left ventricular drain may be inserted into the apex of the left ventricle. The aorta is cross-clamped and a cold cardioplegia solution is pumped into the aortic root causing the heart to be cooled and inducing cardiac arrest. Alternatively, retrograde cardioplegia may be given via the coronary sinus. An incision is made into the left atrium, exposing the damaged mitral valve. The technique so far described is a general description of mitral valve exposure, and is not specific to the particular device.

Surgical techniques of implantation vary between centers. The surgeon will then carefully examine the mitral valve mechanism to ascertain if the valve is amenable to repair, and if so, what the mechanism of repair will be. For example, the lesion may be at the level of the annulus, leaflets, chordae, or papillary muscles. The appropriate surgical repair procedure will depend upon the pathology found. In cases where the annulus is enlarged, or where a segment has been removed from the mitral valve leaflets, the mitral valve annuloplasty ring will be implanted as part of the repair procedure. First the appropriate size ring is chosen using the sizer set supplied for this purpose. Interrupted sutures are placed at the fibrous trigones, between the trigones, and around the remaining circumference of the annulus. The sutures are passed through corresponding portions of the annuloplasty ring, outside the line of demarcation, marked by the colored suture line on the atrial side of the annuloplasty ring. The ring is then pushed down the sutures until it lies on the annulus. Each interrupted suture is tied and cut. Mitral valve competency is then assessed by suitable means (e.g. by the injection of a saline solution through the left ventricular drain, or by removing the aortic cross-clamp and temporarily rendering the aortic valve incompetent). If the mitral valve is regurgitant the areas of reflux are noted. If leakage occurs in the right posterior leaflet, this area of the ring is contracted by gently pulling on one or both of the drawstrings in this region of the ring. It may be necessary to tighten one or both drawstrings, pairs depending upon the individual valve pathology. Mitral valve competence is again assessed, and if necessary further adjustments made.

When the surgeon is satisfied that an optimum mitral valve competence has been achieved without compromising mitral valve opening area the drawstrings are tied as pairs. The surplus portions of the drawstrings are cut close to the knots. Mitral valve competence is then confirmed. At this stage, should any slight reflux be present, it can be eliminated or minimized by placing one or more plicating sutures at the appropriate portion of the annuloplasty ring. However, should a drawstring have been inadvertently over-tightened, it may be cut below the knot to release the constricting segment. That portion of the ring might then need to be shortened by the placement of sufficient plicating sutures. The left atrium is then closed, air removed from the heart, warm blood allowed to reperfuse the coronary tree, the heart defibrillated if necessary, and the patient slowly weaned from cardiopulmonary bypass. Implantation of the tricuspid ring follows a similar course with variations appropriate to the different anatomy and the corresponding differences in the tricuspid and mitral annuloplasty rings.

| References Cited U.S. Pat. Nos. | | |
|---|---|---|
| 3,656,185 | 4/1972 | Carpentier |
| 4,042,979 | 8/1977 | Angell |
| 4,055,861 | 11/1977 | Carpentier et al. |
| 4,164,046 | 8/1979 | Cooley |
| 4,217,665 | 8/1980 | Bex et al. |
| 4,290,151 | 9/1981 | Massana |
| 4,339,831 | 7/1982 | Johnson |
| 4,602,911 | 7/1986 | Ahmadi et al. |
| 4,917,698 | 4/1990 | Carpentier et al. |

Tsakiris AG. "The physiology of the mitral valve annulus". in The mitral valve-a pluridisciplinary approach. ed Kalmanson D. Publishing Sciences Group, Acton, Ma., pg 21, 1976.

Geller M., Kronzon I., Slater J. et al. "Long-term follow-up after mitral valve reconstruction: incidence of postoperative left ventricular outflow obstruction". Circulation, 74:I-99, 1986.

Carpentier A., Deloche A., Hanania G., et al. Surgical management of acquired tricuspid valve disease. J. Thorac Cardiovasc Surg, 67:53, 1974.

Duran C. D., and Ubago J. L. M. "Clinical and Hemodynamic Performance of a Totally Flexible Prosthetic Ring for Atrioventricular Valve Reconstruction" Annals of Thoracic Surgery, 22:458, 1976.

Levine, R. A., Triulzi, M. O., Harrigan P., and Weyman, A. E. "The relationship of mitral annular shape to the diagnosis of mitral valve prolapse", Circulation, 75:756, 1987.

Bex J. P. and Lecompte Y. "Tricuspid valve repair using a flexible linear reducer", J. Cardiac Surg, 1:151, 1986.

What is claimed is:

1. An inplantable annuloplasty ring for use in repairing a human heart valve comprising a ring having a first face constructed and configured to lie, when in use, against an annulus defined by tissue surrounding a human heart valve, and a second face opposite the first face, a major portion of the ring comprising flexible biocompatible contractible fabric, first and second pairs of drawstrings extending through said flexible, biocompatible, contractible fabric, said first and second pair of drawstrings compsising filiform, biocompatible strings, the first pair of drawstring being constructed and positioned to contruct one half of said major portion and the second pair of drawstrings being constructed and adapted to contract the other half of said major portion, whereby drawing either or both of said pairs of drawstrings will cause the ring to contract.

* * * * *